(12) United States Patent
Green

(10) Patent No.: US 6,454,777 B1
(45) Date of Patent: Sep. 24, 2002

(54) APPARATUS AND METHOD FOR SUTURING A BLOOD VESSEL

(76) Inventor: David T. Green, 40 Madison Hill, Fairfield, CT (US) 06430

( * ) Notice: Subject to any disclaimer, the term of this patent is extended or adjusted under 35 U.S.C. 154(b) by 0 days.

(21) Appl. No.: 09/794,553

(22) Filed: Feb. 27, 2001

(51) Int. Cl.[7] ................................................ A61B 17/04
(52) U.S. Cl. .................... 606/144; 606/147; 606/145
(58) Field of Search ............................ 606/144, 147, 606/148, 145, 139

(56) References Cited

U.S. PATENT DOCUMENTS

| | | | |
|---|---|---|---|
| 5,437,681 A | | 8/1995 | Meade et al. |
| 5,540,705 A | | 7/1996 | Meade et al. |
| 5,626,588 A | * | 5/1997 | Sauer et al. ................. 606/144 |
| 5,820,631 A | | 10/1998 | Nobles |
| 5,860,990 A | | 1/1999 | Nobles et al. |
| 5,954,733 A | * | 9/1999 | Yoon ........................... 606/147 |
| 6,238,404 B1 | * | 5/2001 | Hidalgo et al. ............. 606/148 |
| 6,368,334 B1 | * | 4/2002 | Sauer ........................... 606/139 |

FOREIGN PATENT DOCUMENTS

| | | |
|---|---|---|
| DE | 199 42 951 C1 | 9/1999 |
| EP | 0 552 430 A1 | 11/1992 |
| WO | WO 95/13021 | 5/1995 |
| WO | WO 97/27807 | 8/1997 |
| WO | WO 99/04697 | 2/1999 |

* cited by examiner

*Primary Examiner*—Gloria M. Hale
*Assistant Examiner*—Alissa L. Hoey
(74) *Attorney, Agent, or Firm*—Cummings & Lockwood

(57) ABSTRACT

A vascular suturing device is disclosed which includes an elongated tubular body defining opposed proximal and distal end portions and having a longitudinal axis extending therethrough, the body including an inner tubular member, an outer tubular member and a central tubular member disposed between the inner and outer tubular members. The inner tubular member and the central tubular member are mounted for movement relative to the outer tubular member about the longitudinal axis of the body for sequentially driving a pair of suture needles through the wall of a blood vessel to close an incision formed therein.

20 Claims, 12 Drawing Sheets

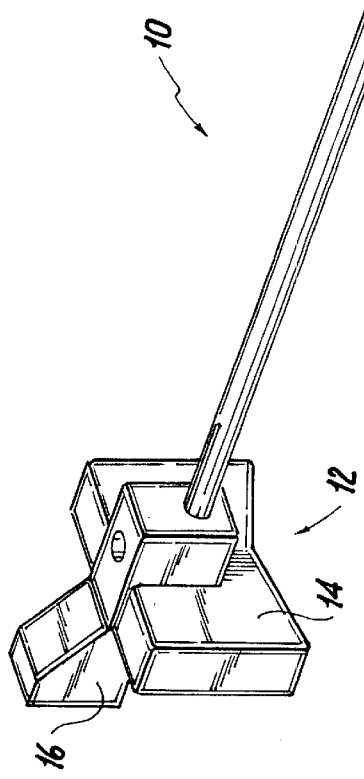
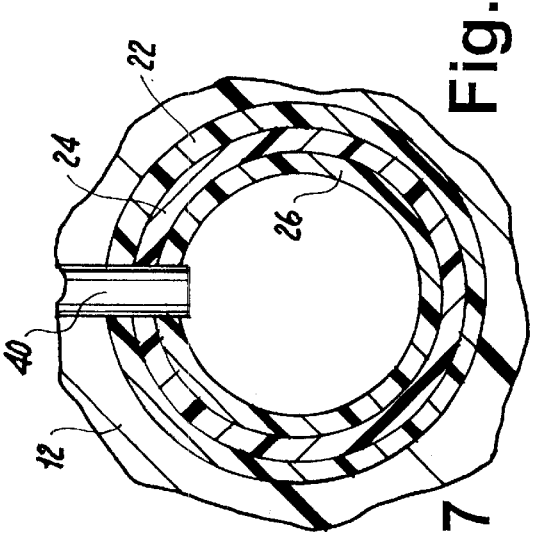
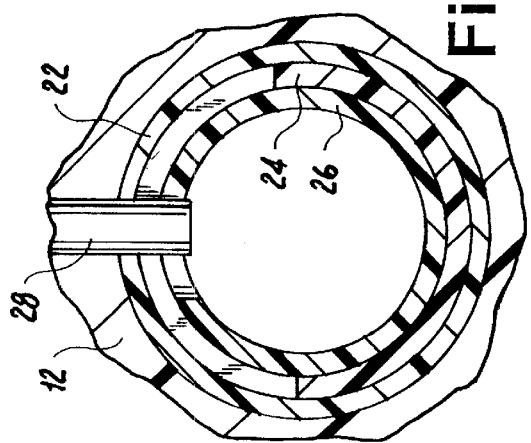

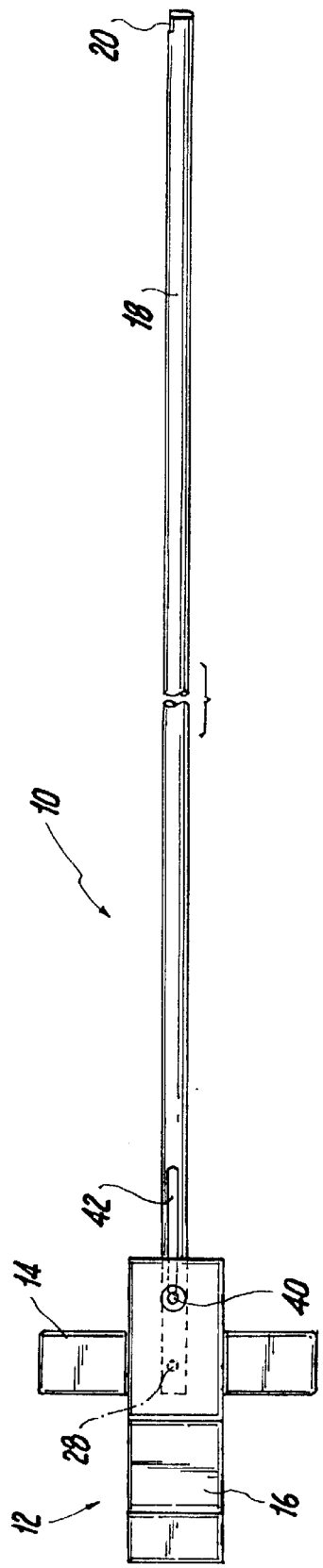
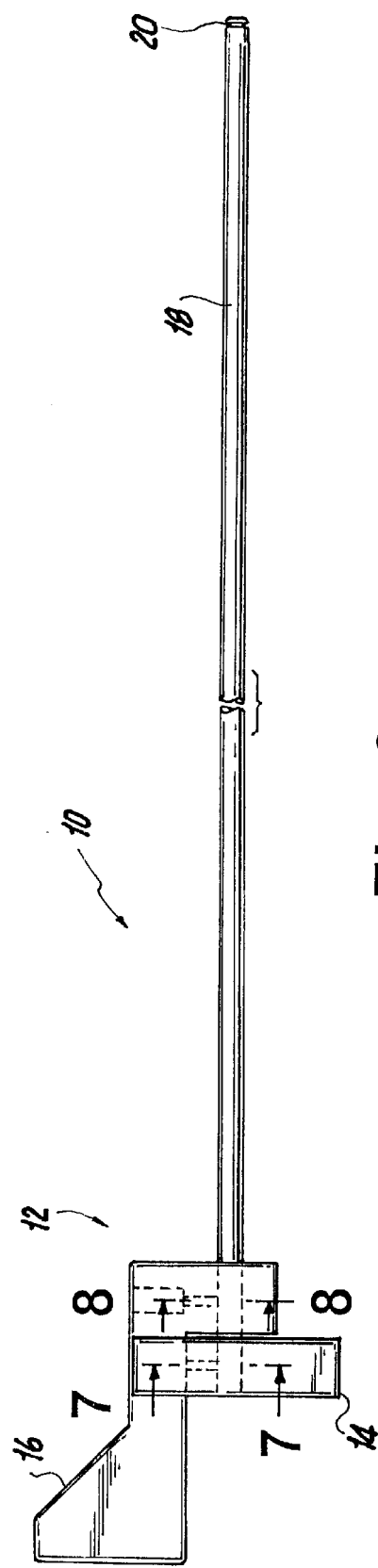
Fig. 2
Fig. 3

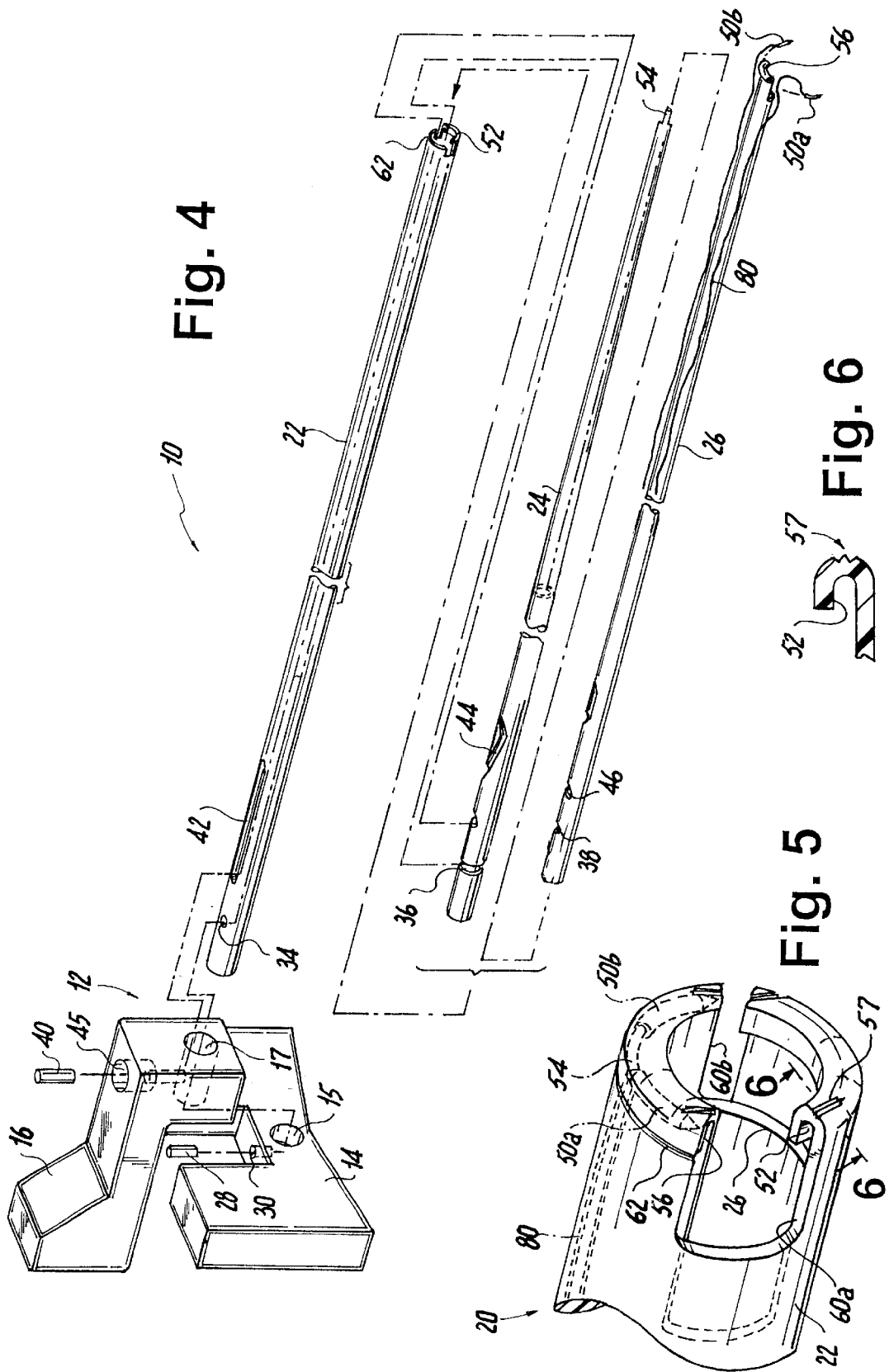

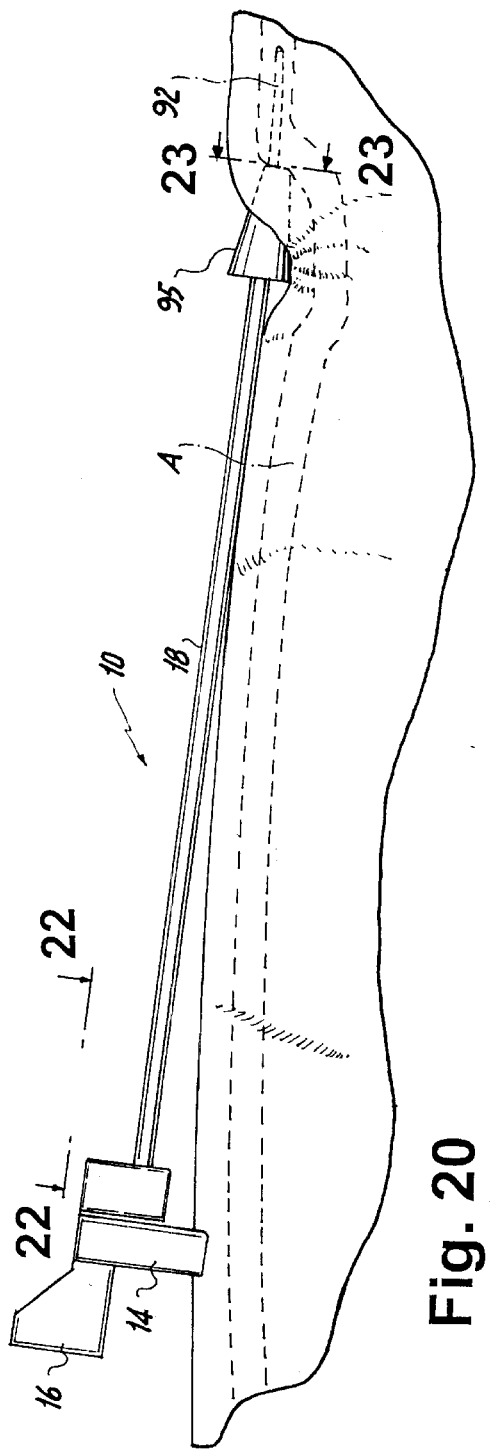
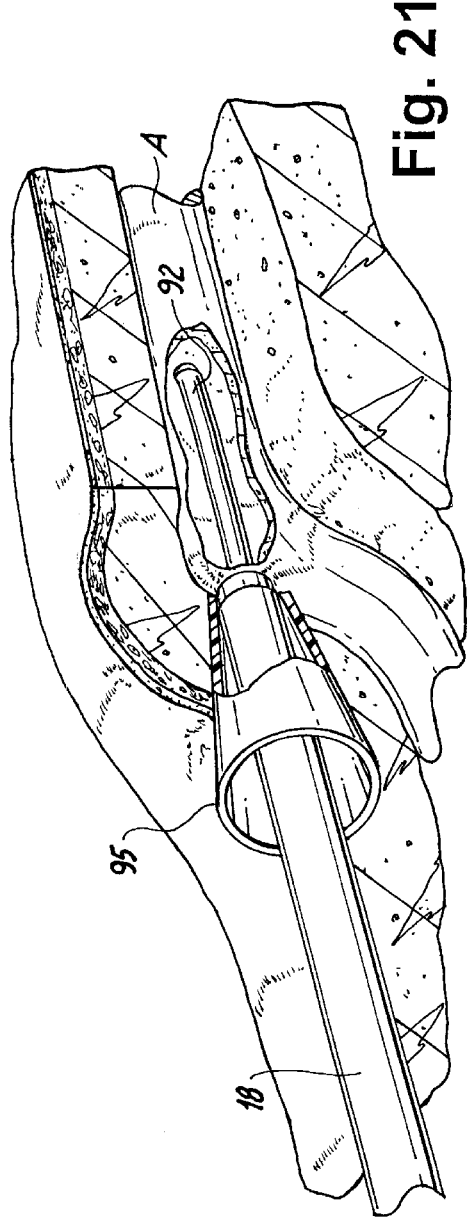

Fig. 22
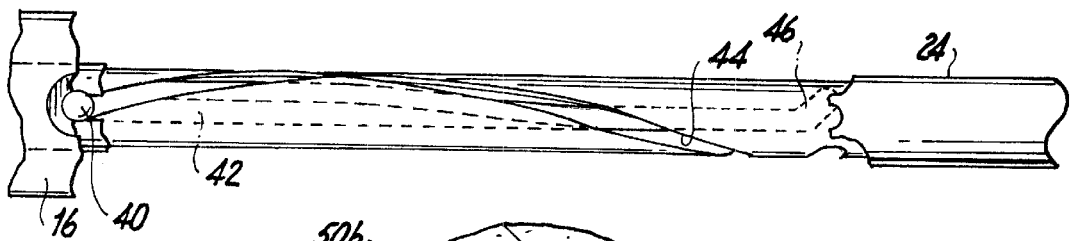
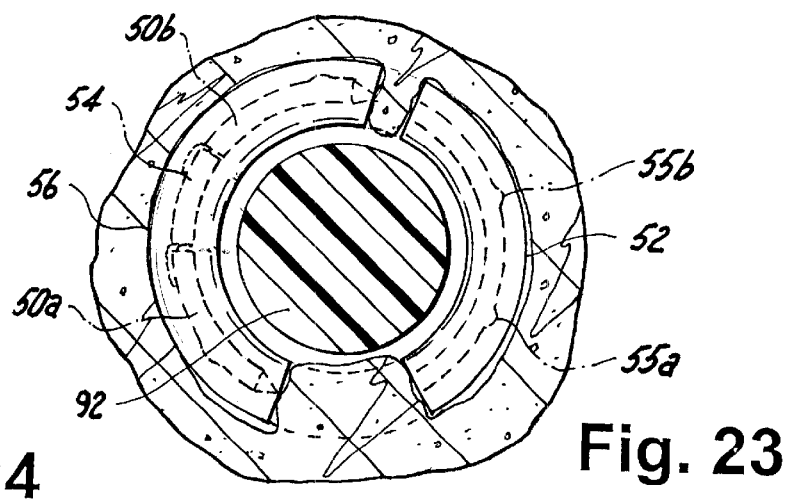
Fig. 24
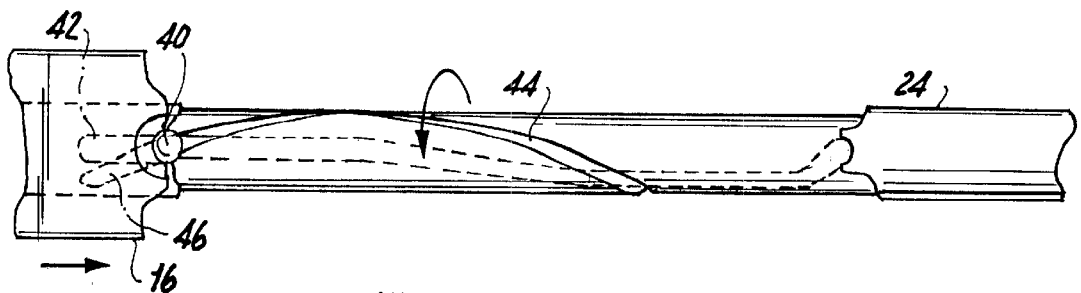
Fig. 23
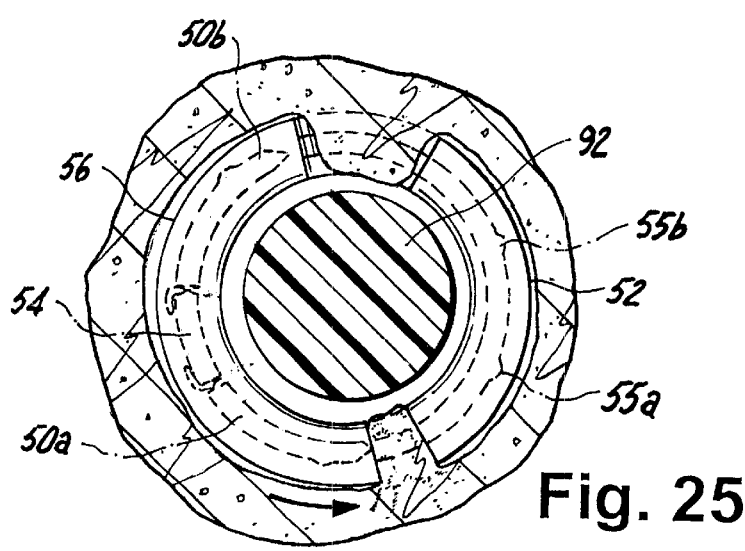
Fig. 25

Fig. 26
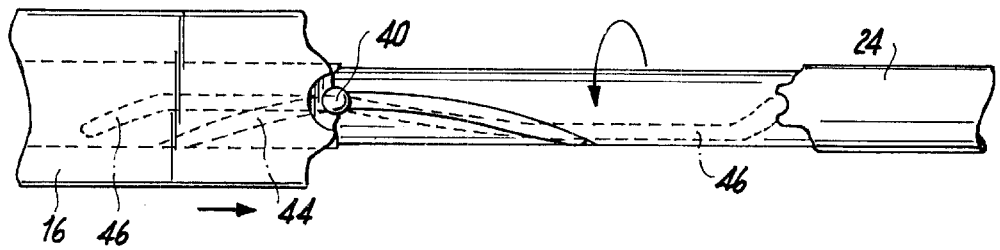
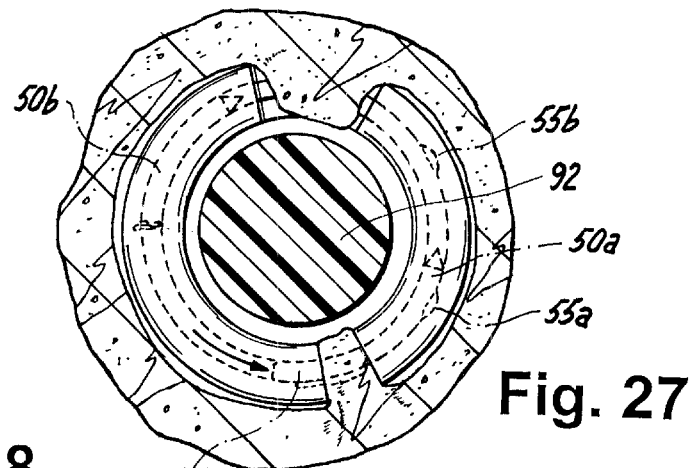
Fig. 27
Fig. 28
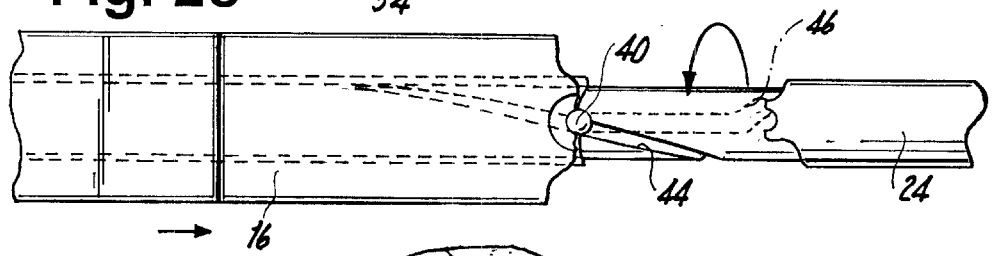
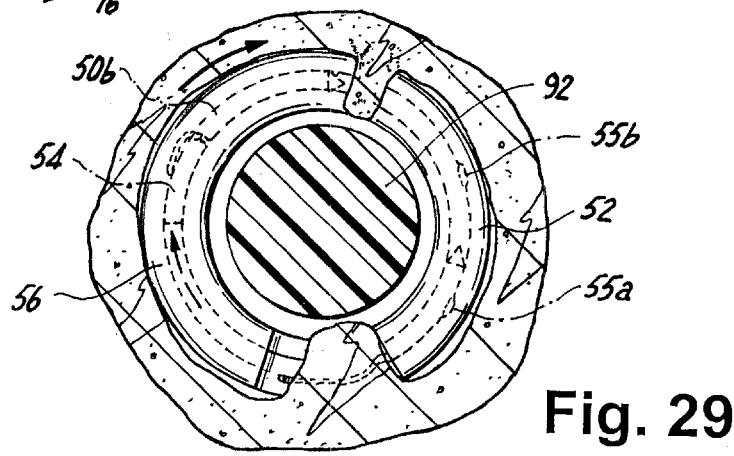
Fig. 29

Fig. 30
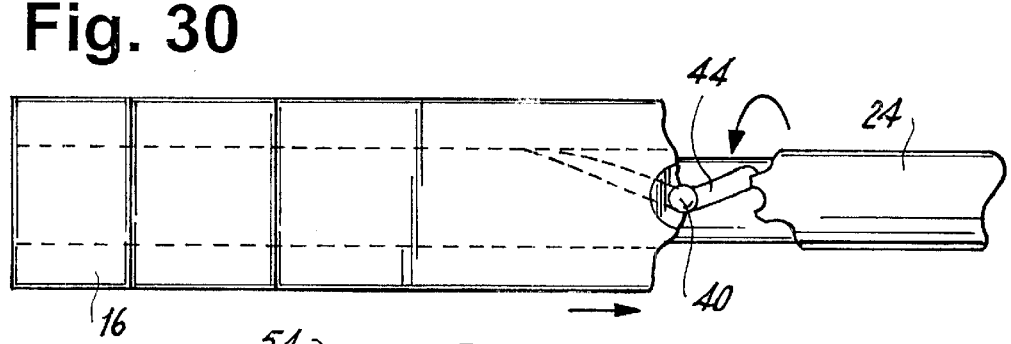
Fig. 32
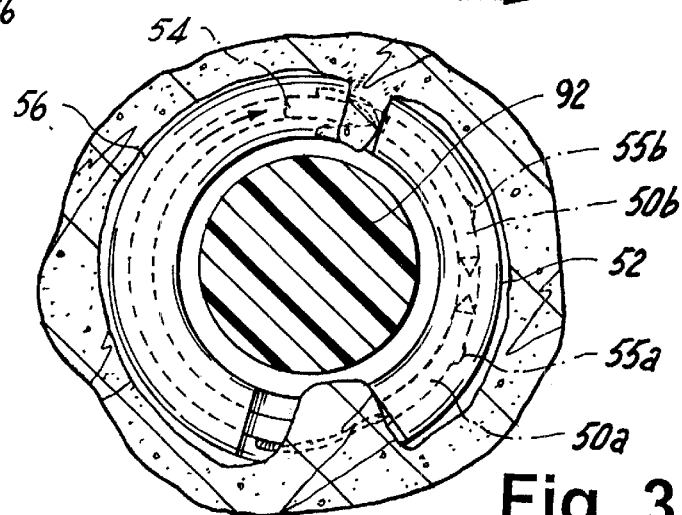
Fig. 31
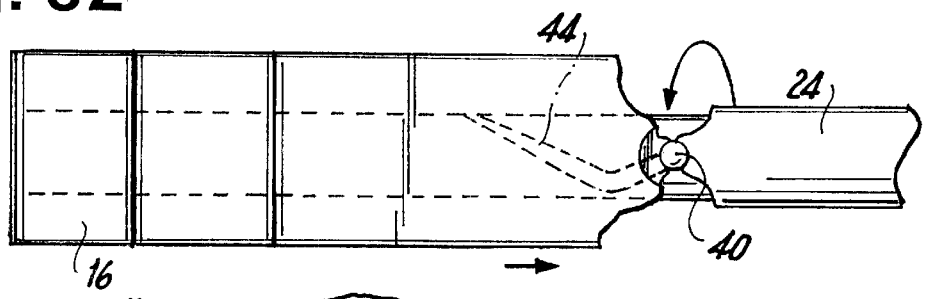
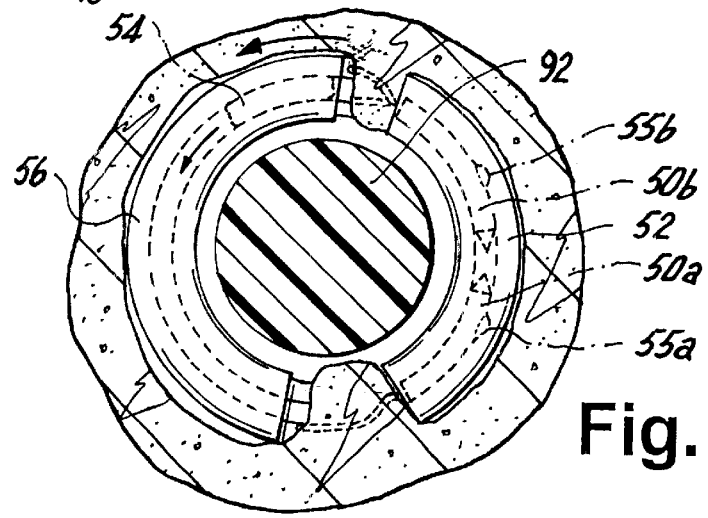
Fig. 33

APPARATUS AND METHOD FOR SUTURING A BLOOD VESSEL

BACKGROUND OF THE INVENTION

1. Field of the Invention

The subject invention is directed to an apparatus and method for closing incisions in blood vessels, and more particularly, to an apparatus and method for percutaneously applying a suture to the wall of a blood vessel to close a surgical incision formed therein.

2. Background of the Related Art

Surgical procedures requiring the introduction of a catheter into a blood vessel, such as the femoral or iliac artery, are well known in the art. Such procedures involve piercing the wall of the blood vessel, inserting an introducer sheath into the opening in the blood vessel, and maneuvering the catheter through the sheath to a target site within the blood vessel. At the conclusion of the procedure, it is necessary to seal the puncture wound in the wall of the blood vessel. It is common to accomplish this by applying direct pressure to the puncture site until homeostasis is achieved. This technique is time consuming, uncomfortable and can cause thrombosis, thereby presenting a danger to the patient.

Consequently, surgical instruments have been developed for suturing a puncture wound in a blood vessel, examples of which are disclosed in U.S. Pat. No. 5,746,755 to Wood et al., U.S. Pat. No. 5,836,955 to Beulna et al., U.S. Pat. No. 5,921,994 to Andreas et al., and U.S. Pat. No. 5,980,539 to Kontos. While these instruments provide improvements over common compression techniques, they remain difficult to use and unable to accomplish the desired task within a relatively short amount of time.

Therefore, it would be beneficial to provide a percutaneously apparatus and method for suturing a puncture wound in the wall of a blood vessel in a relatively short amount of time and with relative ease.

SUMMARY OF THE INVENTION

The subject invention is directed to a new and useful apparatus for percutaneously applying sutures, and more particularly, to an apparatus for closing an incision in the wall of a blood vessel in a relatively short amount of time and with relative ease as compared to prior art devices of its type.

The subject apparatus includes an elongated tubular body defining opposed proximal and distal end portions and having a longitudinal axis extending therethrough. The body includes an inner tubular member, an outer tubular member and a central tubular member disposed between the inner and outer tubular members. The inner tubular member and the central tubular member are mounted for movement relative to the outer tubular member about the longitudinal axis of the body.

The inner tubular member has an arcuate channel formed at the distal end thereof for carrying a pair of arcuate suture needles in back-to-back orientation within a plane extending generally perpendicular to the longitudinal axis of the body. The central tubular member has a distal driving stem extending into the arcuate channel of the inner tubular member and positioned between the pair of suture needles for sequentially driving the suture needles from the arcuate channel of the inner tubular member upon rotation of the central tubular member relative to the inner tubular member. The outer tubular member has an arcuate channel formed at the distal end thereof for receiving the pair of arcuate suture needles after the suture needles have been sequentially driven from the arcuate channel of the inner tubular member by the driving stem of the central tubular member.

An actuator is operatively associated with the proximal end portion of the tubular body for effectuating the relative movement of the inner tubular member and the central tubular member relative to the outer tubular member so as to cause sequential passing of the suture needles from the arcuate channel of the inner tubular member to the arcuate channel of the outer tubular member. Preferably, means are formed within the needle receiving channel of the outer tubular member for securely retaining the suture needles therein, and tissue gripping features are formed on exterior distal surfaces of the outer tubular member.

In accordance with a preferred embodiment of the subject invention, the inner tubular member, the central tubular member and the outer tubular member include cooperating overlying cam slots, and a cam pin extends through the overlying cooperating cam slots to cause the inner tubular member and the central tubular member to rotate relative to the outer tubular member. In addition, a proximal retaining pin is operatively associated with a proximal portion of the elongated tubular body for maintaining the relative axial positions of the outer tubular member, the central tubular inner tubular member and the inner tubular member. The cam pin is operatively connected to the actuator, the actuator is mounted for movement relative to a handle member, and the retaining pin is operatively connected to the handle member.

The subject invention is also directed to a method of suturing the wall of a blood vessel which includes the steps of positioning an elongated tubular body having a longitudinal axis extending therethrough adjacent an incision in the wall of a blood vessel, with the body including a first tubular member and a second tubular member, the first tubular member mounted for movement relative to the second tubular member about the longitudinal axis of the tubular body, and carrying first and second suture needles connected to one another by an elongated suture. The method further includes the sequential steps of passing the first suture needle from the first tubular member, through the wall of the blood vessel, to the second tubular member, and then subsequently passing the second suture needle from the first tubular member, through the wall of the blood vessel, to the second tubular member. The method further includes the steps of withdrawing the elongated tubular body from the wall of the blood vessel, and then tying a knot in the suture to close the incision in the wall of the blood vessel.

These and other aspects of the suturing apparatus and method of the subject invention and the method of using the same will become more readily apparent to those having ordinary skill in the art from the following detailed description of the invention taken in conjunction with the drawings described hereinbelow.

BRIEF DESCRIPTION OF THE DRAWINGS

So that those having ordinary skill in the art to which the subject invention pertains will more readily understand how to make and use the suturing apparatus of the subject invention, preferred embodiments thereof will be described in detail hereinbelow with reference to the drawings, wherein:

FIG. 1 is a perspective view of a vascular suturing device constructed in accordance with a preferred embodiment of the subject invention;

FIG. 2 is a top plan view of the vascular suturing device of FIG. 1;

FIG. 3 is a side elevational view of the vascular suturing device of FIG. 1;

FIG. 4 is an exploded perspective view of the vascular suturing device of FIG. 1 with parts separated for ease of illustration;

FIG. 5 is an enlarged localized perspective view of the distal end portion of the vascular suturing device of FIG. 1;

FIG. 6 is a cross-sectional view of the vascular suturing device taken along line 6—6 of FIG. 5;

FIG. 7 is a cross-sectional view of the vascular suturing device taken along line 7—7 of FIG. 1;

FIG. 8 is a cross-sectional view of the vascular suturing device taken along line 8—8 of FIG. 1;

FIG. 20 illustrates the percutaneous introduction of the vascular suturing device of the subject invention to the incision site of the blood vessel along the path of the stylet positioned in FIG. 19;

FIG. 21 is an enlarged partial cross-sectional view of the distal portion of the vascular suturing device of the subject invention with the wall of the blood vessel engaged thereby;

FIG. 22 is a top plan view of the vascular suturing device of the subject invention as viewed along line 22—22 of FIG. 20 illustrating the initial position of the cam pin within the cam slots of the tubular members;

FIG. 23 is an enlarged front elevational view of the distal end of the vascular suturing device of the subject invention as viewed along line 23—23 of FIG. 20 illustrating the initial back-to-back orientation of the suturing needles disposed in the arcuate needle carrying channel of the inner tubular member;

FIG. 24 is a top plan view of the vascular suturing device of the subject invention as viewed along line 22—22 of FIG. 20 illustrating a second position of the cam pin within the cam slots of the tubular members;

FIG. 25 is an enlarged front elevational view of the distal end of the vascular suturing device of the subject invention as viewed along line 23—23 of FIG. 20 when the inner tubular member rotates in a counter clock-wise direction relative to the outer tubular member so as to clamp the wall of the blood vessel between grasping surfaces of the inner and outer tubular members;

FIG. 26 is a top plan view of the vascular suturing device of the subject invention as viewed along line 22—22 of FIG. 20 illustrating a third position of the cam pin within the cam slots of the tubular members;

FIG. 27 is an enlarged front elevational view of the distal end of the vascular suturing device of the subject invention as viewed along line 23—23 of FIG. 20 when the first suturing needle is driven from the needle carrying channel of the inner tubular member by the needle driving stem of the central tubular member, through the clamped blood vessel wall and into the needle receiving channel of the outer tubular member;

FIG. 28 is a top plan view of the vascular suturing device of the subject invention as viewed along line 22—22 of FIG. 20 illustrating a fourth position of the cam pin within the cam slots of the tubular members;

FIG. 29 is an enlarged front elevational view of the distal end of the vascular suturing device of the subject invention as viewed along line 23—23 of FIG. 20 when the driving stem of the central tubular member and the inner tubular member are rotated in a clock-wise direction relative to the outer tubular member so as to position the driving stem behind the second suturing needle and to clamp the blood vessel wall between grasping surfaces of the inner and outer tubular members;

FIG. 30 is a top plan view of the vascular suturing device of the subject invention as viewed along line 22—22 of FIG. 20 illustrating a fifth position of the cam pin within the cam slots of the tubular members;

FIG. 31 is an enlarged front elevational view of the distal end of the vascular suturing device of the subject invention as viewed along line 23—23 of FIG. 20 when the second suturing needle is driven from the needle carrying channel of the inner tubular member by the needle driving stem of the central tubular member, through the clamped blood vessel wall and into the needle receiving channel of the outer tubular member;

FIG. 32 is a top plan view of the vascular suturing device of the subject invention as viewed along line 22—22 of FIG. 20 illustrating a sixth position of the cam pin within the cam slots of the tubular members;

FIG. 33 is an enlarged front elevational view of the distal end of the vascular suturing device of the subject invention as viewed along line 23—23 of FIG. 20 when the driving stem of the central tubular member and the inner tubular member are rotated in a counter clock-wise direction relative to the outer tubular member so as to release the clamped blood vessel wall.

DETAILED DESCRIPTION OF PREFERRED EMBODIMENTS

Figure 9:
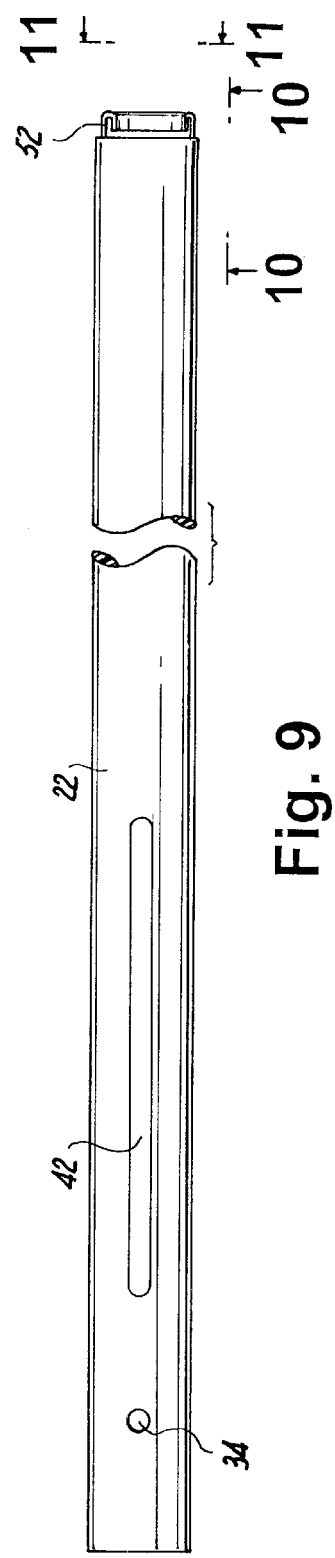
FIG. 9 is a top plan view of the outer tubular member of the vascular suturing device of FIG. 1 illustrating the elongated cam slot defined therein and the arcuate needle receiving channel formed at the distal end thereof.

Referring now to the drawings wherein like reference numerals identify similar structural elements of the apparatus disclosed herein, there is illustrated in FIG. 1 a vascular suturing device constructed in accordance with a preferred embodiment of the subject invention and designated generally by reference numeral 10. In the specification that follows the term "distal" shall refer to the end of the vascular suturing device that is nearest to the surgical site, while the term "proximal" shall refer to the end of the vascular suturing device that is farthest from the surgical site.

Referring now to FIGS. 1–3, 7 and 8, vascular suturing device 10 includes a proximal handle portion 12 having a stationary support portion 14 and a translating actuation portion 16. The components of handle portion 12 are preferably formed from a high strength thermoplastic material such as, for example, Lexan®. Support portion 14 is ergonomically configured to be positioned on a patient's leg during a vascular closure procedure. An elongated tubular body portion 18 extends from a bore 15 in support portion 14, through an elongate passage 17 in actuation portion 16, and includes a distal suture applying portion 20, which is shown specifically in the localized view of FIG. 5. It is envisioned that the distal suture applying portion could be constructed as a replaceable cartridge configured for mounting at the distal end of the body portion.

Body portion 18 has three relatively movable concentric tubular members which are illustrated in FIG. 4 in an unassembled condition. These members include an outer tubular member 22, an inner tubular 26 and a central tubular member 24 disposed between the inner and outer tubular members 22 and 26. One or more of the tubular components of body portion 18 are preferably formed from stainless steel, or a similar bio-compatible material.

Figure 15:
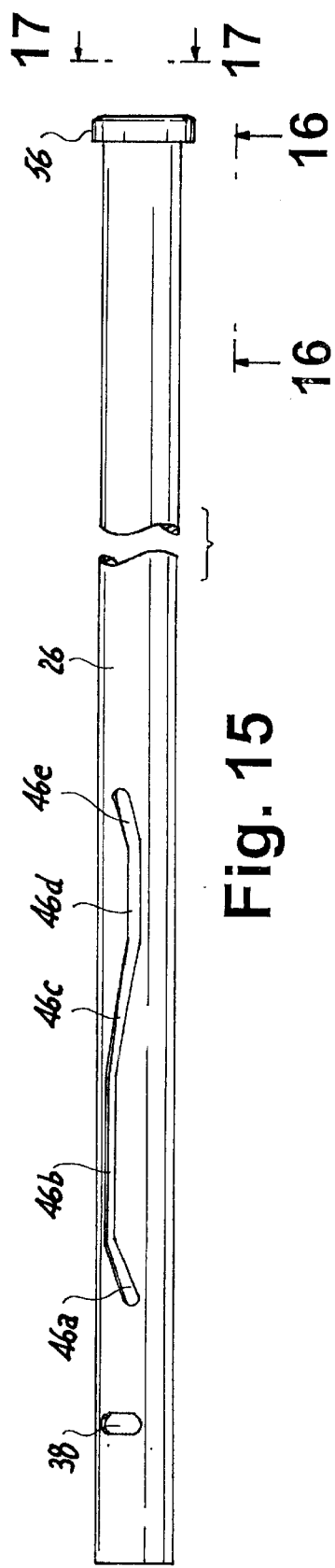
FIG. 15 is a top plan view of the inner tubular member of the vascular suturing device of FIG. 1 illustrating the stepped cam slot defined therein and the arcuate needle carrying channel formed at the distal end thereof.

As best seen in FIGS. 3 and 7, a proximal positioning pin 28 extends through a countersunk transverse bore 30 in support portion 14 for engaging an aperture 34 in the proximal end portion of outer tubular member 22 (see FIG. 9). Positioning pin 28 also engages a relatively large arcuate slot 36 in the proximal potion of central tubular member 24 (see FIGS. 12 and 13), and a relatively small arcuate slot 38 in the proximal portion of inner tubular member 26 (see FIG. 15). Proximal positioning pin 28 is adapted and configured to maintain the relative axial positions of the three tubular members.

As best seen in FIGS. 3 and 8, a distal cam pin 40 extends through a countersunk transverse bore 45 in actuation portion 16 for engaging a linear cam slot 42 formed in outer tubular member 22 (see FIG. 9). Cam pin 40 also engages a first stepped cam slot 44 in central tubular member 24 (see FIG. 12), and a second stepped cam slot 46 is inner tubular member 26 (see FIG. 15). Distal cam pin 40 is adapted and configured to effectuate the relative axial rotation of the three concentric tubular members of body portion 18 as it translates in a distal direction through the cooperating superimposed, overlying cam slots 42, 44 and 46, of tubular members 22, 24 and 26, respectively, under the guidance of the translating actuation portion 16.

Figure 11:
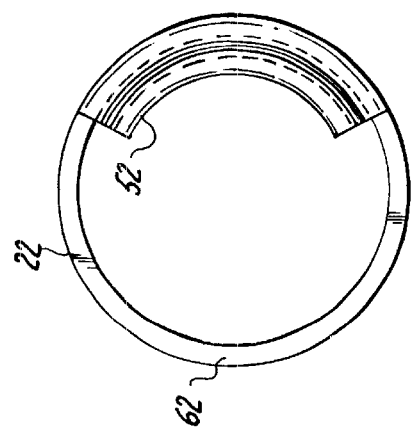
FIG. 11 is an enlarged front elevational view of the distal end portion of the outer tubular member of FIG. 9 as viewed along line 11—11 of FIG. 9.
Figure 17:
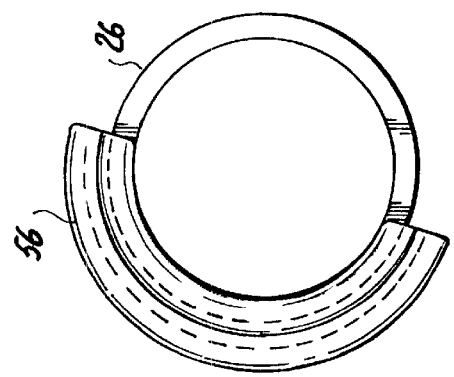
FIG. 17 is an enlarged front elevational view of the distal end portion of the inner tubular member of FIG. 15 as viewed along line 17—17 of FIG. 15.

Referring now to FIGS. 4 and 5, the distal suture applying portion 20 of suturing apparatus 10 is defined in part by a U-shaped annular channel 52 formed at the distal end of outer tubular member 22 (see FIG. 11), and in part by a U-shaped annular channel 56 formed at the distal end of inner tubular member 26 (see FIG. 17). As discussed in greater detail hereinbelow, the arcuate channel 56 of inner tubular member 26 defines a needle carrying channel for carrying a pair of curved suture needles 50a and 50b disposed in back-to-back orientation in a plane extending perpendicular to the longitudinal axis of the tubular body portion 18. The arcuate channel 52 of outer tubular member defines a needle receiving channel for receiving suture needles 50a and 50b after they have been sequentially driven through the wall of a blood vessel during a vascular suturing procedure.

Figure 14:
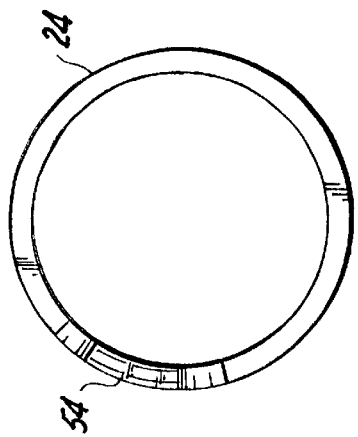
FIG. 14 is an enlarged front elevational view of the distal end portion of the central tubular member of FIG. 12 as viewed along line 14—14 of FIG. 12.

As best seen in FIG. 5, a depending distal wall portion 62 of outer tubular member 22 (see FIG. 10) abuts the upturned wall of needle carrying channel 56 to enclose the curved suture needles therein. In addition, FIG. 5 illustrates the position of the distal driving stem 54 of central tubular member 22 (see FIG. 14) which extends into the needle carrying channel 56 of inner tubular member 26 between the adjacent rear ends of the suture needles 50a and 50b for sequentially driving the suture needles therefrom during a vascular suturing procedure. FIG. 5 also illustrates the diametrically opposed tissue reception areas 60a and 60b that are formed at the distal end of body portion 18 for receiving or gathering-up the wall of a blood vessel. In addition, as illustrated in FIGS. 5 and 6, the terminal radial edges of arcuate channels 52 and 56 are provided with ridged or textured gripping surfaces 57 that extend generally perpendicular to the edges of the channels for gripping the wall of a blood vessel during a suturing procedure.

Figure 10:
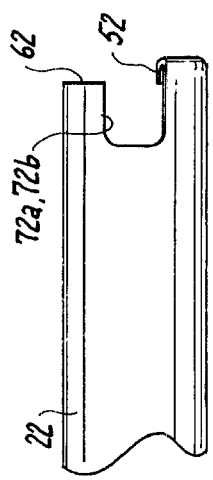
FIG. 10 is an enlarged side elevational view of the distal end portion of the outer tubular member of FIG. 9 as views along line 10—10 of FIG. 9.
Figure 12:
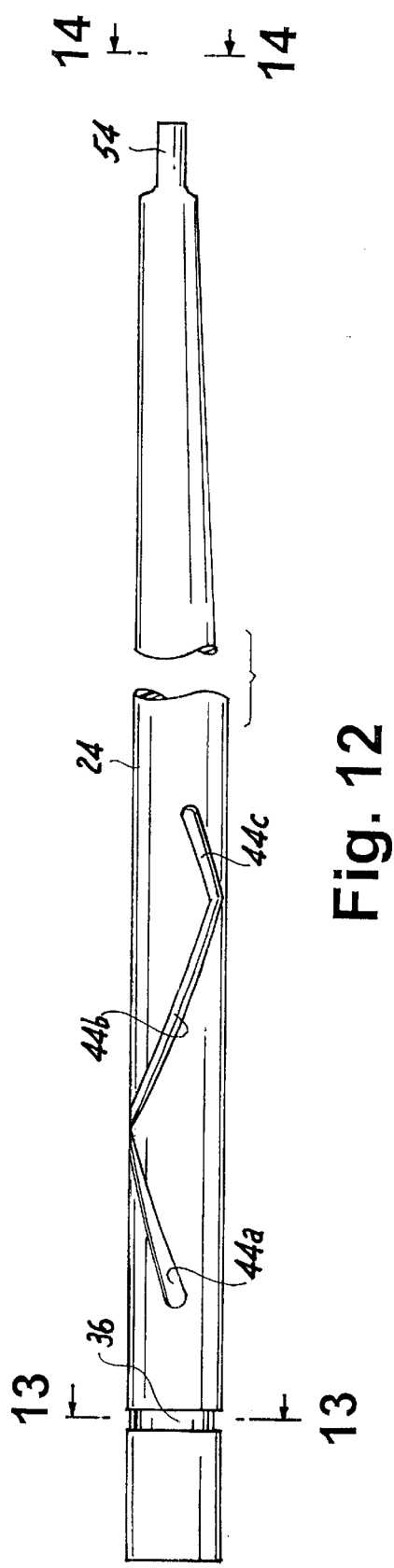
FIG. 12 is a top plan view of the central tubular member of the vascular suturing device of FIG. 1 illustrating the stepped cam slot defined therein and the needle driving stem formed at the distal end thereof.
Figure 13:
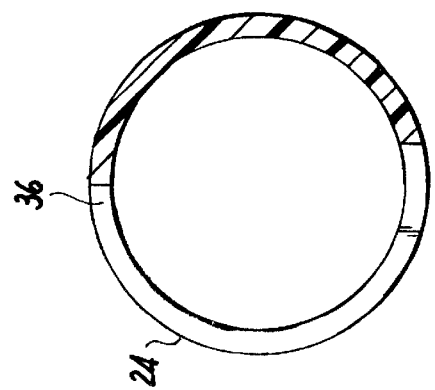
FIG. 13 is an enlarged cross-sectional view of the central tubular member of FIG. 12 taken along line 13—13 of FIG. 12.
Figure 16:
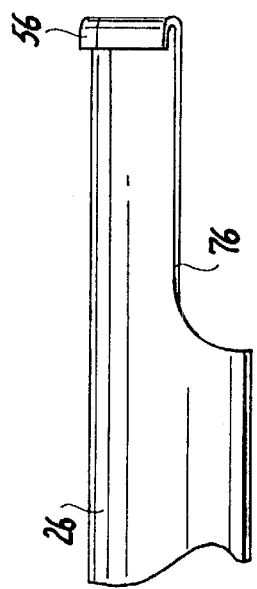
FIG. 16 is an enlarged side-elevational view of the distal end portion of the inner tubular member of FIG. 15 as viewed along line 16—16 of FIG. 15.

Referring now to FIG. 4, the relatively movable concentric tubular members of body portion 18 are uniquely configured to operate in conjunction with one another during a vascular suturing procedure. In particular, the outer tubular member 22 has a uniform cross-sectional configuration along its length, as does the inner tubular member 26. In contrast, as shown in FIG. 12, the central tubular member 24 is partially tapered or truncated along a portion of its length so as to accommodate the structural features of the inner tubular member 26 as it is received therein. As best seen in FIG. 10, the distal end portion of outer tubular member 22 has diametrically opposed recesses 72a and 72b which define part of the tissue reception areas 60a and 60b shown in FIG. 5. Similarly, FIG. 16 illustrates an undercut 76 formed at the distal end of inner tubular member 26 which also defines part of the tissue engagement areas 60a and 60b.

FIG. 4 also illustrates the suture 80 that extends between the two curved suture needles 50a and 50b disposed within needle carrying channel 56. Suture 80 may be of braided or monofilament construction, and can be absorbable or non-absorbable. It is normally stored within the space defined by the truncated area of central tubular member 24, and can extend to the exterior of the instrument through an aperture (not shown) formed in tubular body 18 such that the free ends thereof are easily accessible by the surgeon.

Referring now to FIG. 9, as noted above, the outer tubular member 22 has a linear cam slot 42 for cooperating with cam pin 40 and an aperture 34 for receiving positioning pin 28. Consequently, axial movement of actuator 16 during a suturing procedure does not cause any rotational movement of outer tubular member 22. In contrast, referring to FIG. 15, inner tubular member 26 has a stepped cam slot 46 for cooperating with cam pin 40 and a relatively short arcuate slot 38 for accommodating positioning pin 28. Cam slot 46 has four inflection points defining five distinct slot sections for effectuating the rotational movement of inner tubular member 26 relative to the outer tubular member 22, and more particularly, for sequentially approximating circumferentially adjacent terminal ends of the arcuate channels 52 and 56 of the outer and inner tubular members 22 and 26 so as to clamp portions of the wall of a punctured blood vessel therebetween.

In particular, cam slot 46 has a first helical section 46a that facilitates rotational movement of the inner tubular member 26 in a first direction through a first angle of rotation; a first linear section 46b corresponding to a first dwell period in which the inner tubular member 26 does not rotate about its axis; a second helical section 46c that facilitates rotational movement of the inner tubular member 26 in a second direction through a second angle of rotation; a second linear section 46d corresponding to a second dwell period in which the inner tubular member 26 does not rotate about its axis; and a third helical section 46e that facilitates rotational movement of the inner tubular member 26 in the first direction through a third angle of rotation.

Referring now to FIG. 12, the central tubular member 24 has a stepped cam slot 44 for cooperating with cam pin 40 and a relatively long arcuate slot 36 for accommodating positioning pin 28. Cam slot 44 has two inflection points defining three distinct slot sections for effectuating the rotational movement of inner tubular member 24 relative to the outer tubular member 22, and more particularly, for sequentially driving the curved suture needles 50a and 50b from needle carrying channel 56 of inner tubular member 26.

In particular, cam slot 44 has a first helical section 44a that facilitates rotational movement of the central tubular member 24 in a first direction through a first angle of rotation during which the driving stem 54 drives a first curved suture needle from needle carrying channel 56; a second helical section 44b that facilitates rotational movement of the central tubular member 24 in a second direction through a second angle of rotation during which the driving stem 54 drives a second curved suture needle from needle carrying channel 56; and a third helical section 44c that facilitates rotational movement of the central tubular member 24 in the first direction through a third angle of rotation to reposition the driving stem 54 of central tubular member 44 in a neutral position within needle carrying channel 56 of inner tubular member 26.

As discussed in detail hereinbelow with respect to FIGS. 20 through 34, the rotational movements of the central and inner tubular members 24 and 26, and the dwell periods of the inner tubular member 26 effectuated by the translation of the cam pin 40 through the cooperating superimposed cam slots 44 and 46 correspond to sequential steps in the suturing methodology of the subject invention.

Figure 18:
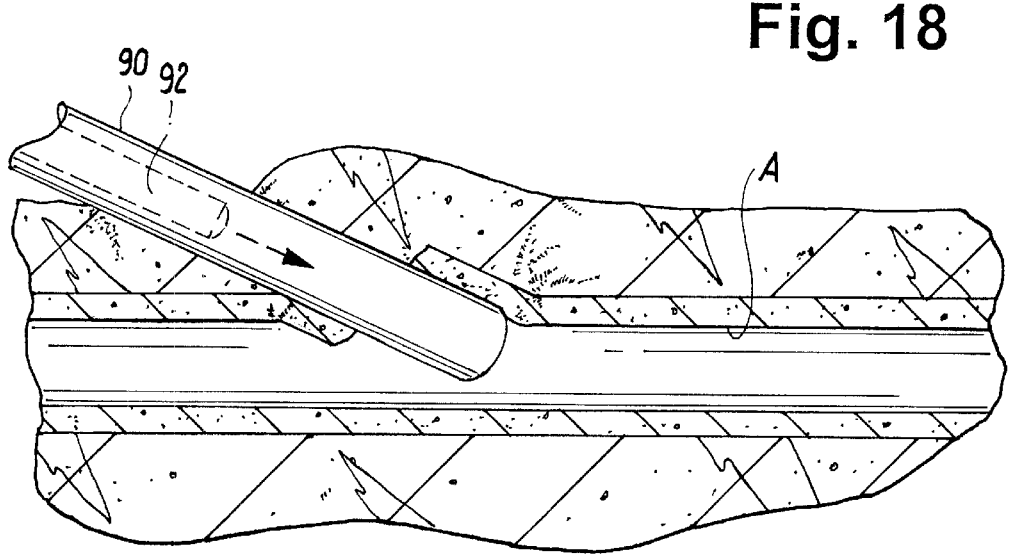
FIG. 18 illustrates a tubular cannula extended through an incision in the wall of a blood vessel, as a flexible stylet is introduced therethrough.
Figure 19:
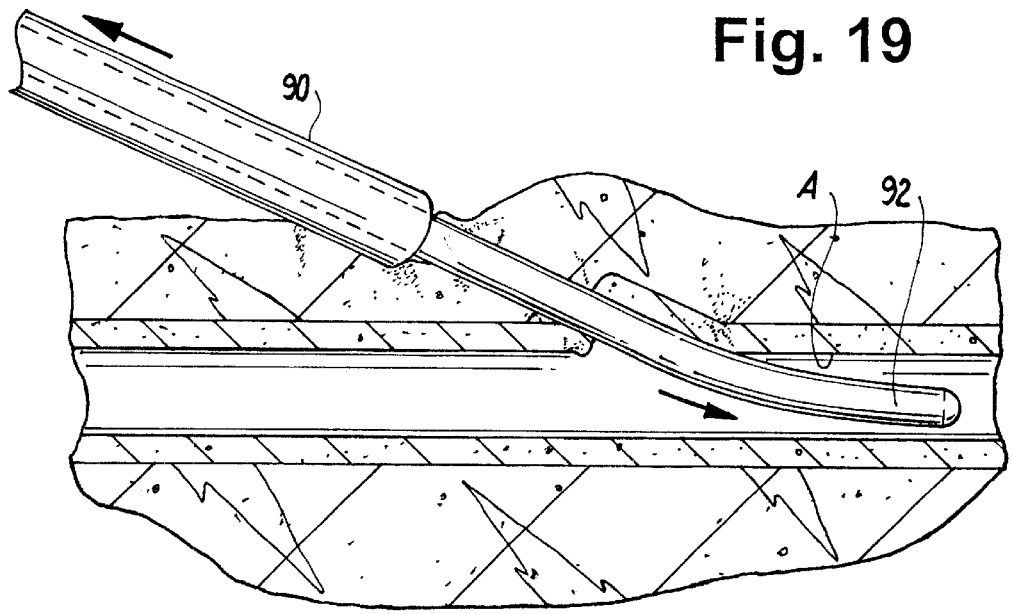
FIG. 19 illustrates a flexible stylet extended into the blood vessel as the tubular cannula is removed from the incision site.

In use, at the conclusion of a surgical procedure conducted through an incision or puncture wound in the wall of a blood vessel, such as the femoral artery, a tubular cannula 90 is utilized to facilitate the percutaneous introduction of a flexible stylet 92 into the lumen of the blood vessel A, as illustrated in FIG. 18. Thereafter, as shown in FIG. 19, the tubular cannula 90 is removed from the incision site. Then, the vascular suturing device 10 of the subject invention, with the aide of an optional tapered nose piece 95, is percutaneously introduced to the surgical site as it is guided along the stylet by way of the central lumen of body portion 18, as illustrated in FIGS. 20 and 21.

Referring to FIGS. 22 and 23, upon commencing the vascular suturing procedure of the subject invention, the cam pin 40 is in an initial position within the superimposed cam slots 42, 44 and 46 of tubular members 22, 24 and 26, respectively. This corresponds to the initial position of the suturing needles 50a and 50b within the arcuate needle carrying channel 56 of the inner tubular member 26, with the distal driving stem 54 of central tubular member 24 disposed therebetween.

Thereafter, when, through manipulation of actuation handle 16 relative to stationary handle portion 14, cam pin 40 is moved to the second position of FIG. 24, it has translated through the first helical section 46a of cam slot 46 in inner tubular member 26 to the first inflection point. This causes the inner tubular member 26 to rotate in a counter-clockwise direction relative to the outer tubular member 22 so as to clamp the wall of the blood vessel within engagement area 60a between grasping surfaces of the arcuate channels 52 and 56 of outer and inner tubular members 22 and 26, as shown in FIG. 25. At the same time, the cam pin 40 has traveled partially through the first helical section 44a of cam slot 44 in central member 24, so as to cause the central tubular member 24 follow the inner tubular member 26 in the counter-clockwise direction.

When the cam pin 40 is disposed in the third position of FIG. 26, it has traveled through the first linear section 46b of cam slot 46 in inner tubular member 26 to the second inflection point thereof, and through the remainder of the first helical section 44a of cam slot 44 in central tubular member 24 to the first inflection point thereof. This causes the inner tubular member 26 to remain stationary during the first dwell period, and causes the central tubular member 24 to continue to rotate in a counter-clockwise direction relative to the inner tubular member 26. Consequently, the first suturing needle 50a is driven from the needle carrying channel 56 of the inner tubular member 26 by the needle driving stem 54 of the central tubular member 24, through the clamped blood vessel wall and into the needle receiving channel 52 of the outer tubular member 22, where it is captured by a retention structure 55a, such as a protuberance depending from the wall of channel 52, as shown in FIG. 27.

Later, when the cam pin 40 is disposed in the fourth position of FIG. 28, it has traveled through the second helical section 46c of cam slot 46 of inner tubular member 26 to the third inflection point thereof, and partially through the second helical section 44b of cam slot 44 in central tubular member 24. This causes, the inner tubular member 26 to rotate in a clockwise direction relative to the outer tubular member 22 so as to clamp the blood vessel wall within tissue engagement area 60b between adjacent grasping surfaces of the outer and inner tubular members 22 and 26, as shown in FIG. 29. At the same time, the central tubular member 26 rotates in a clockwise direction so as to move into a driving position behind the second curved suturing needle 50b in needle carrying channel 56 of inner tubular member 26.

Thereafter, when the cam pin 40 is disposed in the fifth position of FIG. 30, it has traveled through the second linear section 46d of cam slot 46 of inner tubular member 26 to the fourth inflection point thereof, and through the reminder of the second helical section 44b of central tubular member 24. This causes the inner tubular member 26 to remain stationary during the second dwell period, while the central tubular member 24 continues to rotate in a clockwise direction such the distal driving stem 54 drives the second suturing needle 50b from the needle carrying channel 56 of the inner tubular member 26, through the clamped blood vessel wall and into the needle receiving channel 52 of the outer tubular member 22, where it is captured by retention structure 55b, as shown in FIG. 31. Although the retention structures 55a and 55b are shown as protuberances, other structures may be provided to retain the suture needles. For example, the width of the channel could gradually reduce in size to capture the suture needles.

When the cam pin 40 is in the sixth position of FIG. 32, it has traveled completely through the linear cam slot 42 of outer tubular member 22, through the third helical section 46e of cam slot 46 of inner tubular member 26, and through the third helical section 44c of cam slot 44 in central tubular member 24. This causes the inner tubular member 26 to rotate in a counter-clockwise direction to release the wall of the blood vessel and causes the central tubular member 24 to rotate in a counter clockwise direction so as to move the distal driving stem 54 into a neutral position within the needle carrying channel 56 of inner tubular member 26, as shown in FIG. 33.

Figure 34:
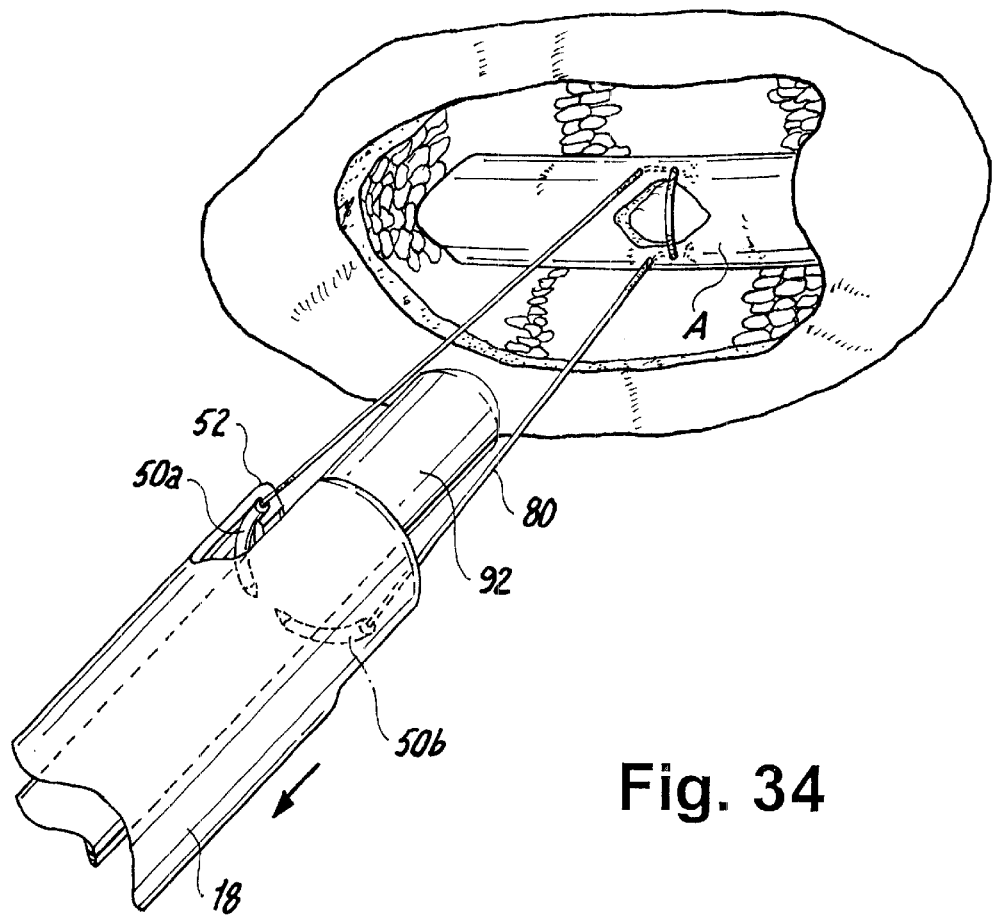
FIG. 34 illustrates the removal of the vascular suturing device of the subject invention as it is withdrawn from the incision site carrying the suturing needles therewith.

Referring now to FIG. 34, at the conclusion of the needle driving sequence described hereinabove, the vascular suturing device 10 of the subject invention is withdrawn from the incision site carrying the captured suturing needles 50a and 50b therewith. Thereafter, the free ends of suture 80 are gathered by the surgeon and a knot is tied therein so as to close the puncture wound in the wall of the blood vessel.

Although the vascular suturing apparatus and method of the subject invention has been described with respect to preferred embodiments, those skilled in the art will readily appreciate that changes and modifications may be made thereto without departing from the spirit and scope of the present invention.

What is claimed is:

1. A vascular suturing device comprising:
   a) an elongated tubular body defining opposed proximal and distal end portions and having a longitudinal axis extending therethrough, the body including an inner tubular member, an outer tubular member and a central tubular member disposed between the inner and outer tubular members, the inner tubular member and the central tubular member mounted for movement relative to the outer tubular member about the longitudinal axis of the tubular body, and wherein:
      i) the inner tubular member has an arcuate channel formed at the distal end thereof for carrying a pair of arcuate suture needles in back-to-back orientation within a plane extending generally perpendicular to the longitudinal axis of the body;
      ii) the central tubular member has a distal driving stem extending into the arcuate channel of the inner tubular member and positioned between the pair of suture needles for sequentially driving the suture needles from the arcuate channel of the inner tubular member upon rotation of the central tubular member relative to the inner tubular member; and
      iii) the outer tubular member has an arcuate channel formed at the distal end thereof for receiving the pair of arcuate suture needles after the suture needles have been sequentially driven from the arcuate channel of the inner tubular member by the driving stem of the central tubular member; and
   b) an actuator operatively associated with the proximal end portion of the tubular body for effectuating the relative movement of the inner tubular member and the central tubular member relative to the outer tubular member so as to cause sequential passing of the suture needles from the arcuate channel of the inner tubular member to the arcuate channel of the outer tubular member.

2. A vascular suturing device as recited in claim 1, wherein means are formed within the needle receiving channel of the outer tubular member for securely retaining the suture needles therein.

3. A vascular suturing device as recited in claim 1, wherein the inner tubular member, the central tubular member and the outer tubular member include cooperative overlying cam slots, and a cam pin extends through the cooperative overlying cam slots to cause the inner tubular member and the central tubular member to rotate relative to the outer tubular member.

4. A vascular suturing device as recited in claim 3, wherein a proximal retaining pin is operatively associated with a proximal portion of the elongated tubular body for maintaining relative axial positions of the outer tubular member, the central tubular member and the inner tubular member.

5. A vascular suturing device as recited in claim 4, wherein the proximal portions of each one of the outer tubular member, the central tubular member and the inner tubular member include means for accommodating the proximal retaining pin.

6. A vascular suturing device as recited in claim 4, wherein the cam pin is operatively connected to the actuator.

7. A vascular suturing device as recited in claim 6, wherein the actuator is mounted for movement relative to a handle member.

8. A vascular suturing device as recited in claim 7, wherein the retaining pin is operatively connected to the handle member.

9. A vascular suturing device as recited in claim 1, further comprising a pair of arcuate suture needles, and an elongated suture extending between the pair of arcuate suture needles.

10. A vascular suturing device as recited in claim 1, wherein tissue gripping features are formed on exterior distal surfaces of the outer tubular member.

11. A vascular suturing device comprising:
    a) an elongated tubular body defining opposed proximal and distal end portions and having a longitudinal axis extending therethrough, the body including an inner tubular member, an outer tubular member and a central tubular member disposed between the inner and outer tubular members, the inner tubular member and the central tubular member mounted for movement relative to the outer tubular member about the longitudinal axis of the tubular body, and wherein:
       i) the inner tubular member has an arcuate channel formed at the distal end thereof, and a pair of arcuate suture needles are carried within the arcuate channel in back-to-back orientation disposed in a plane extending generally perpendicular to the longitudinal axis of the body;
       ii) the central tubular member has a distal driving stem extending into the arcuate channel of the inner tubular member and positioned between the pair of suture needles for sequentially driving the suture needles from the arcuate channel of the inner tubular member upon rotation of the central tubular member relative to the inner tubular member; and
       iii) the outer tubular member has an arcuate channel formed at the distal end thereof for receiving the pair of arcuate suture needles after the suture needles have been sequentially driven from the arcuate channel of the inner tubular member by the driving stem of the central tubular member; and
    b) camming means for effectuating the relative movement of the inner tubular member and the central tubular member relative to the outer tubular member so as to cause sequential passing of the suture needles from the arcuate channel of the inner tubular member to the arcuate channel of the outer tubular member.

12. A vascular suturing device as recited in claim 11, wherein retaining means are formed within the needle receiving channel of the outer tubular member for securely retaining the suture needles therein.

13. A vascular suturing device as recited in claim 11, wherein the camming means includes a cam slot formed in each one of the inner tubular member, the central tubular member and the outer tubular member, the cam slots in each of the tubular members cooperating with a cam pin extending therethrough to cause the inner tubular member and the central tubular member to rotate relative to the outer tubular member.

14. A vascular suturing device as recited in claim 13, wherein a proximal retaining pin is operatively associated with a proximal portion of the elongated tubular body for maintaining relative axial positions of the outer tubular member, the central tubular member and the inner tubular member.

15. A vascular suturing device as recited in claim 14, wherein the proximal portions of each one of the outer tubular member, the central tubular member and the inner tubular member include means for accommodating the proximal retaining pin.

16. A vascular suturing device as recited in claim 14, wherein the cam pin is operatively connected to an actuator, and wherein the actuator is mounted for movement relative to a handle member.

17. A vascular suturing device as recited in claim 16, wherein the retaining pin is operatively connected to the handle member.

18. A method of suturing comprising the steps of:
a) positioning a distal end portion of an elongated tubular body having a longitudinal axis extending therethrough adjacent an incision in a wall of a blood vessel, the body including a first tubular member and a second tubular member, the first tubular member mounted for movement relative to the second tubular member about the longitudinal axis of the tubular body, and carrying first and second suture needles connected to one another by an elongated suture;
b) passing the first suture needle from the first tubular member, through the wall of the blood vessel, to the second tubular member;
c) passing the second suture needle from the first tubular member, through the wall of the blood vessel, to the second tubular member; and
d) withdrawing the elongated tubular body from the wall of the blood vessel.

19. A method according to claim 18, further comprising the step of tying a knot in the suture to close the incision in the wall of the blood vessel.

20. A method according to claim 18, further comprising the step of guiding the elongated tubular body to the incision in the wall of the blood vessel over a stylet.

\* \* \* \* \*